United States Patent [19]

Boroschewski et al.

[11] 4,252,557

[45] Feb. 24, 1981

[54] M-DIURETHANES

[75] Inventors: Gerhard Boroschewski; Friedrich Arndt, both of Berlin, Fed. Rep. of Germany

[73] Assignee: Schering Aktiengesellschaft, Berlin and Bergkamen, Fed. Rep. of Germany

[21] Appl. No.: 47,126

[22] Filed: Jun. 11, 1979

Related U.S. Application Data

[63] Continuation of Ser. No. 657,503, Feb. 12, 1976, abandoned, which is a continuation of Ser. No. 496,238, Aug. 9, 1974, abandoned.

[30] Foreign Application Priority Data

Aug. 10, 1974 [DE] Fed. Rep. of Germany ....... 2341079

[51] Int. Cl.$^3$ ...................... A01N 47/18; A01N 47/20
[52] U.S. Cl. ........................................ 71/100; 71/111

[58] Field of Search ................................. 71/100, 111

[56] References Cited

U.S. PATENT DOCUMENTS

| | | | |
|---|---|---|---|
| 3,124,446 | 3/1964 | Cameron | 71/122 |
| 3,404,975 | 10/1968 | Wilson et al. | 71/100 |
| 3,558,685 | 1/1971 | Osieka et al. | 71/100 |
| 3,687,997 | 8/1972 | Kiehs et al. | 71/100 |
| 3,746,741 | 7/1973 | Hubele | 71/111 |
| 3,792,994 | 2/1974 | Baker et al. | 71/111 |

FOREIGN PATENT DOCUMENTS 2109798 8/1972 Fed. Rep. of Germany ............ 71/100

*Primary Examiner*—Glennon H. Hollrah
*Attorney, Agent, or Firm*—Michael J. Striker

[57] ABSTRACT

New m-diurethanes having selective herbicidal action are provided, including their preparation.

10 Claims, No Drawings

M-DIURETHANES

This application is a continuation of Application Ser. No. 657,503, filed Feb. 12, 1976 which was a continuation of Application Ser. No. 496,238, filed Aug. 9, 1974, both now abandoned.

The invention relates to new m-diurethanes, selective herbicides containing these compounds as active ingredients, and to methods for their manufacture.

m-Diurethanes with selective herbicidal effect are known German Disclosures No. 1,567,151 and 1,568,621. Of these compounds, methyl-N-(3-(N-(3-methylphenyl)-carbamoyloxy)-phenyl) carbamate (Phenmedipham) has attained great practical importance. This agent, however, develops its excellent selective herbicidal effect predominantly in post-emergence.

It is an object of the present invention to provide a selective weed control agent which can be used successfully chiefly in pre-emergence.

According to the present invention the problem is solved by an agent which is characterized by a content of at least one compound of the general formula

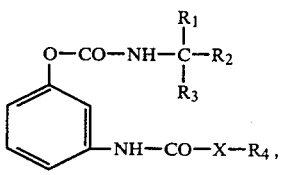

in which $R_1$ is hydrogen or an alkyl radical with 1 to 3 carbon atoms, $R_2$, is a saturated or unsaturated hydrocarbon radical with 1 to 4 carbon atoms, $R_3$, is an alkyl radical with 1 to 3 carbon atoms, $R_1$ and $R_3$ together with the carbon atom represent a cycloaliphatic hydrocarbon radical with 5 or 6 carbon atoms, and $R_4$, is an alkyl radical with 1 to 3 carbon atoms, while x is oxygen or sulfur.

The agent of the invention is effective especially when used in pre-emergence against many weeds, of which the following may be named: *Stellaria media, Senecio vulgaris, Matricharia chamomilla, Lamium amplexicaule, Centaurea cyanus, Amarantus retroflexus, Chrysanthemum segetum, Ipomea purpurea, Polygonum lapathifolium, Avena fatua, Alopecurus myosuroides, Echinochloa crus galli, Setaria italica* and *Setaria faberi.*

The agent is extraordinarily selective and leaves crop plants undamaged, which are not required even at applied quantities up to 5 kg/ha or more. Thus the agent can be used selectively for weed control in pre-emergence in soybeans, tomatoes, carrots, cotton, potatoes, corn and peanut cultivations, this being of particular advantage.

The herbicidal effect of the agent according to the invention exerts itself also against weeds when used in post-emergence and is then also selective in relation to some crop cutivation, such as, peanut, corn and rice, so that the spectrum of application of this agent is surprisingly broad.

The applied quantities for selective weed control are in general 0.5–5 kg of active ingredient per hectare.

The compounds of the invention can be used either alone, in mixture with one another, or in mixture with other active substances. If desired, other plant protection or pest control agents, e.g. fungicides, nematocides or other agents, may be added according to the desired purpose. An addition of fertilizers is also feasible for use with the compounds.

If a broadening of the spectrum effect is intended, other herbicides may also be added; although then the selectivity is not always preserved, depending on the nature of the mixture partner. As herbicidal mixture partners that are suitable are active ingredients from the groups of the carbamic acid and thiocarbamic acid esters, of the substituted anilins and anilides, triazines, aminotriazoles, diazines, as well as uracils, such as, 3-cyclohexyl-5,6-trimethyl-enuracil, 1-phenyl-4-amino-5-chloropyridazone (6), aliphatic carboxylic acids and phenylacetic acids, aryl-oxycarboxylic acids, e.g. hydrazides, amides, nitriles, halogen carboxylic acids, such as, 2,2-dichloropropionic acid or the salts thereof, esters of such carboxylic acids, ureas, 2,3,6-trichlorobenzyloxypropanol, rhodanium-containing agents and others.

Depending on the purpose of use other substances may also be added, by which must be understood for example also non-phytotoxic additions which may have a synergistic effect with herbicides, such as wetting agents, emulsifiers, solvents, oily additions and others.

Expediently, the effective substances of the invention are used in the form of preparations, such as powders, scatters, granulates, solutions, emulsions or suspensions, with the addition of liquid and/or solid vehicles or diluents singly or jointly and possibly wetting, adhesive, emulsifying and/or dispersing aids.

Suitable liquids used as vehicles are; for example, water, aliphatic and aromatic hydrocarbons, such as benzene, toluene, xylene, cyclohexanone, isophorone, and mineral oil fractions.

As suitable solid vehicles are mineral earths; such as siliceous clay, silica gel, talc, kaolin, attaclay, limestone, silicic acid and plant products, like flours.

Among the surface active substances that may be named are: calcium-lignin sulfonate, polyoxyethylene-octylphenol ether, naphthalene-sulfonic acids, phenol-sulfonic acids, formaldehyde condensates, fatty alcohol sulfates and fatty acid alkalis and alkaline earth salts.

It has been found, surprisingly, that the herbicidal effect and the selectivity of the agents can be increased when they contain the surface-active substances in proportions higher than the usual quantities.

The proportion of active substance or substances in the various preparations may vary in a wide range. For example, the agents contain about 20 to 80 percent by weight of active substances, about 80 to 20 percent by weight of liquid or solid vehicles and possibly up to 30 percent by weight of surface-active substances.

The activation of the agents can be carried out in a known manner, such as by mixing or grinding. If desired, the single components may alternatively be mixed just before their use, as is done in the practice known in so-called tank mixing.

The new compounds of the invention may be produced by methods known in themselves. This is done, for example, by reacting (a) compounds of the general formula

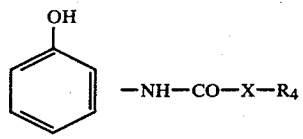

with an isocyanate of the general formula

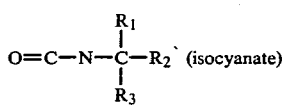

expediently with addition of a tertiary organic base, as for example triethylamine, or a tin-organic compound, such as dibutyl tin dilaurate, or by reacting (b) compounds of the general formula

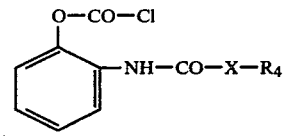

with an amine of the general formula

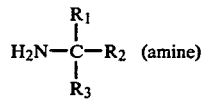

in the presence of an acid acceptor, e.g. with addition of excess amine or an inorganic or tertiary organic base, such as soda lye, sodium carbonate, potassium carbonate or triethylamine, and isolating the process products in a manner known, $R_1$, $R_2$, $R_3$, $R_4$ and X having the above stated meaning.

The following example will explain the production of the compounds of the invention:

1.

Ethyl-N-(3-(N-(1,1-dimethylpropinyl)-carbamoyloxy)-phenyl)-carbamate

Into a solution of 5.0 g (0.06 mole) of 1,1-dimethylpropinylamine in 30 ml acetic ester is dropped, after addition of 50 ml water, at 10° to 15° C., while stirring, a solution of 14.6 g (0.06 mole) chloroformic acid-3-(N-carbethoxyamino)-phenyl ester in 30 ml acetic ester and simultaneously a solution of 8.3 g (0.06 mole) potassium carbonate in 30 ml water, the reaction product crystallizing out. Stirring is continued for 30 minutes while cooling with ice. The product is suction-filtered and washed with ether and water.

Yield: 13.6 g=78% of the theory.

In an analogous manner the following compounds can be produced:

| Name of Compound | | Physical constant |
|---|---|---|
| 2. | Methyl-N-(3-(N-1,2-dimethylpropyl)-carbamoyloxy)-phenyl)-carbamate | M.p. 140–141° C. |
| 3. | Methyl-N-(3-(N-(1-ethylpropyl)-carbamoyloxy)-phenyl)-carbamate | M.p. 162–164° C. |
| 4. | Methyl-N-(3-(N-(1,1-diethylpropinyl)-carbamoyloxy)-phenyl)-carbamate | M.p. 129–130° C. |
| 5. | Methyl-N-(3-(N-(1,1-dimethylpropyl)carbamoyloxy)-phenyl)-carbamate | M.p. 126–127° C. |
| 6. | Methyl-N-(3-(N-(1,1-dimethylpropinyl)-carbamoyloxy)-phenyl)-carbamate | M.p. 147–150° C. |
| 7. | Ethyl-N-(3-(N-(1,1-diethylpropinyl)-carbamoyloxy)-phenyl)-carbamate | M.p. 120–121° C. |
| 8. | Ethyl-N-(3-(N-(1,1-dimethylpropyl)-carbamoyloxy)-phenyl)-carbamate | M.p. 130–131° C. |
| 9. | S-Methyl-N-(3-(N-(1,1-diethylpropinyl)-carbamoyloxy)-phenyl)-thiocarbamate | M.p. 119–122° C. |
| 10. | S-Methyl-N-(3-(N-(1,1-dimethylpropyl)-carbamoyloxy)-phenyl)-thiocarbamate | M.p. 164–166° C. |
| 11. | Methyl-N-(3-(N-(1-ethinylcyclohexyl)-carbamoyloxy)-phenyl)-carbamate | M.p. 117–119° C. |
| 12. | Isopropyl-N-(3-(N-(1,1-diethyl-2-propinyl)-carbamoyloxy)-phenyl)-carbamate | M.p. 112–114° C. |
| 13. | Isopropyl-N-(3-(N-(1,1-dimethyl-2-propinyl)-carbamoyloxy)-phenyl)-carbamate | M.p. 133–134° C. |
| 14. | Isopropyl-N-(3-(N-(1,1-dimethyl-propyl)-carbamoyloxy)-phenyl)-carbamate | M.p. 142–143° C. |
| 15. | Isopropyl-N-(3-(1-methylbutyl)-carbamoyloxy)-phenyl)-carbamate | M.p. 152–153° C. |
| 16. | S-Ethyl-N-(3-(N-(1-ethinylcyclohexyl)-carbamoyloxy)-phenyl)thiocarbamate | M.p. 117–118° C. |
| 17. | S-Ethyl-N-(3-(N-(1,1-diethylpropinyl)-carbamoyloxy)-phenyl)thiocarbamate | M.p. 127–128° C. |
| 18. | S-Ethyl-N-(3-(N-(1,1-dimethylpropinyl)-carbamoyloxy)-phenyl)thiocarbamate | M.p. 122–123° C. |
| 19. | S-Ethyl-N-(3-(N-(1-methylbutyl)-carbamoyloxy)-phenyl)thiocarbamate | M.p. 118–119° C. |
| 20. | S-Ethyl-N-(3-(N-(1-ethylpropyl)-carbamoyloxy)-phenyl)thiocarbamate | M.p. 153–155° C. |
| 21. | S-Methyl-N-(3-(N-(1-ethinylcyclohexyl)-carbamoyloxy)-phenyl)thiocarbamate | M.p. 115–117° C. |
| 22. | S-Methyl-N-(3-(N-(1-ethylpropyl)-carbamoyloxy)-phenyl)thiocarbamate | M.p. 139–141° C. |

These compounds are soluble in acetone, cyclohexanone, isophorone and tetrahydrofurance, with the possibility of greatly increasing the solubility by the addition of a little dimethyl formamide or hexamethyl phosphoric acid triamide. They are practically insoluble in water and light benzine.

The following examples will explain the invention.

EXAMPLE 1

In Sown Seeds of the plant species listed in the following table were sown in loamy soils. After seeding, the mentioned active substances were sprayed as pre-emergence herbicides in an applied quantity of 1 kg of active substance per hectare, emulsified in 500 ltr water/hectare. The plants emerged after 10 days. Four weeks after the spraying, the results of the treatment were evaluated by rating with the value scale 0="totally destroyed" to 10="not damaged". It was found that the compounds of the invention destroyed the weeds without harming the cultivation, while the comparison agent was not effective.

| Agent of invention | Applied quantity in kg active substance/ha | soy-bean | cot-ton | pea-nut | po-tato | corn | rice | Stel-laria media | Sen-ecio vul-garis | Matri-caria cham-omilla | Lam-ium am-plexi-caule | Cen-tau-rea cyanus | Ama-rantus retro-flexus | Chry-san-the-mum se-getum | Ipomea pur-purea | Poly-gonum lapa-thi-folium | Avena fatua | Alope-curus myosur-oides | Echi-no-chloa crus galli | Se-taria ital-ica | Se-taria fa-beri |
|---|---|---|---|---|---|---|---|---|---|---|---|---|---|---|---|---|---|---|---|---|---|
| 1. Methyl-N-(3-(N-(1,2-dimethyl-propyl)-carbamoyloxy)-phenyl)-carbamate | 1 | — | — | 10 | 10 | — | 10 | 0 | 0 | 0 | 0 | 0 | 0 | 0 | — | — | — | — | 0 | 0 | — |
| 2. Methyl-N-(3-(N-(1-ethylpropyl)-carbamoyloxy)-phenyl)-carbamate | 1 | — | — | 10 | 10 | — | 10 | 0 | 0 | 0 | 0 | 0 | 0 | 0 | 0 | 0 | 0 | 1 | 0 | 0 | 1 |
| 3. Methyl-N-(3-(N-(1,1-diethyl-propinyl)-carbamoyloxy)-phenyl)-carbamate | 1 | — | — | 10 | — | 10 | 10 | 0 | — | — | — | — | — | — | — | 0 | 0 | 0 | 0 | 0 | — |
| 4. Methyl-N-(3-(N-(1,1-dimethyl-propyl)-carbamoyloxy)-phenyl)-carbamate | 1 | — | — | 10 | 10 | — | 10 | 0 | — | — | — | — | — | 1 | — | 1 | — | 1 | 2 | 4 | 3 |
| 5. Methyl-N-(3-(N-(1,1-dimethyl-propinyl)-carbamoyloxy)-phenyl)-carbamate | 1 | — | — | 10 | 10 | 10 | 10 | 0 | 0 | 0 | 0 | 0 | 0 | 0 | 0 | 0 | 1 | 1 | 1 | 4 | 0 |
| 6. Ethyl-N-(3-(N-(1,1-diethyl-propinyl)-carbamoyloxy)-phenyl)-carbamate | 1 | 10 | — | 10 | 10 | 10 | 10 | 0 | — | — | 0 | 0 | 0 | 0 | 0 | 0 | 1 | 1 | 0 | 0 | 0 |
| 7. Ethyl-N-(3-(N-(1,1-dimethyl-propinyl)-carbamoyloxy)-phenyl)-carbamate | 1 | 10 | 10 | 10 | 10 | 10 | 10 | 0 | — | — | 1 | 3 | 0 | — | 0 | 1 | — | — | — | — | 3 |
| 8. Ethyl-N-(3-(N-(1,1-dimethyl-propyl)-carbamoyloxy)-phenyl)-carbamate | 1 | 10 | 10 | 10 | 10 | 10 | 10 | 0 | 3 | 0 | 0 | 2 | 0 | 3 | 0 | 2 | — | — | — | — | — |
| 9. S-Methyl-N-(3-(N-(1,1-diethyl-propinyl)-carbamoyloxy)-phenyl)-thiocarbamate | 1 | 10 | 10 | 10 | 10 | 10 | 10 | 0 | — | 0 | 1 | 3 | 0 | — | 0 | 1 | — | — | — | — | 4 |
| 10. S-Methyl-N-(3-(N-(1,1-dimethyl-propinyl)-carbamoyloxy)-phenyl)-thiocarbamate | 1 | 10 | 10 | 10 | 10 | 10 | 10 | 1 | — | 0 | 0 | — | 1 | — | — | — | — | — | — | — | — |
| 11. Isopropyl-N-(3-(N-(1,1-diethyl-2-propinyl)-carbamoyloxy)phenyl)-carbamate | 1 | 10 | 10 | 10 | 10 | 10 | 10 | 0 | — | 0 | 0 | 0 | 0 | 4 | 0 | 0 | 0 | — | 3 | 3 | — |
| 12. Isopropyl-N-(3-(N-(1,1-dimethyl-2-propinyl)-carbamoyloxy)phenyl)-carbamate | 1 | 10 | 10 | 10 | 10 | 10 | — | 0 | — | 4 | 0 | 0 | 3 | — | — | 3 | — | — | — | — | — |
| 13. Isopropyl-N-(3-(N-(1,1-dimethyl-propyl)-carbamoyloxy)-phenyl)-carbamate | 1 | 9 | 10 | 10 | 10 | 10 | 9 | 4 | — | 0 | 1 | 0 | 0 | 0 | 1 | 0 | — | — | — | 5 | — |
| 14. Isopropyl-N-(3-(N-(1-methyl-butyl)-carbamoyloxy)-phenyl)-carbamate | 1 | 9 | 10 | 10 | 10 | 10 | 10 | 4 | — | 2 | 3 | 1 | 6 | — | 1 | 3 | — | — | — | — | — |
| 15. Methyl-N-(3-(N-(1-ethinyl-cyclohexyl)-carbamoyloxy)-phenyl)-carbamate | 1 | 9 | 9 | — | 10 | 10 | 10 | 0 | 0 | 0 | 0 | 0 | 0 | 0 | 0 | 0 | — | — | — | — | — |

-continued

| | Applied quantity in kg active substance/ha | soy-bean | cot-ton | pea-nut | po-tato | corn | rice | Stel-laria media | Sen-ecio vul-garis | Matri-caria cham-omilla | Lam-ium am-plexi-caule | Cen-tau-rea cyanus | Ama-rantus retro-flexus | Chry-san-the-mum se-getum | Ipomea pur-purea | Poly-gonum lapa-thi-folium | Avena fatua | Alope-curus myosur-oides | Echi-no-chloa crus galli | Se-taria ital-ica | Se-taria fa-beri |
|---|---|---|---|---|---|---|---|---|---|---|---|---|---|---|---|---|---|---|---|---|---|
| Comparison agent Methyl-N-(3-(N-(3-methyl-phenyl)-carbamoyloxy)-phenyl)-carbamate | 1 | 10 | 10 | 10 | 10 | 10 | 10 | 5 | 10 | 10 | 9 | 10 | 10 | 10 | 10 | 10 | 10 | 10 | 10 | 10 | 10 |

EXAMPLE 2

The plants listed in the following table were treated with the designated agent in a young stage after formation of the first foliage leaves. The applied quantity was 1 kg of active substance/ha. emulsified in 500 ltr water per hectare. The evaluation was made 14 days after the treatment, by rating according to Example 1. In this post-emergence treatment the agents of the invention again destroyed the weeds without harm to the crop plants. The comparison agent showed no effect.

| Agent of invention | Applied quantity of kg active substance/ha | Cotton | Peanut | Corn | Rice | Stellaria media | Senecio vulgaris | Matricaria chamomilla | Lamium amplexicaule | Centaurea cyanus | Chrysanthemum segetum | Ipomea purpurea | Polygonum lapathiofolium | Echinochloa crus galli | Setaria italica | Setaria faberi | Amarantus retroflexus |
|---|---|---|---|---|---|---|---|---|---|---|---|---|---|---|---|---|---|
| 1. Methyl-N-(3-(N-(1,2-dimethyl-propyl)-carbamoyloxy)-phenyl-carbamate | 1 | — | 10 | — | — | 0 | — | 0 | 0 | 0 | 0 | 0 | — | 0 | 0 | — | 0 |
| 2. Methyl-N-(3-(N-(1-ethyl-propyl)-carbamoyloxy)-phenyl-carbamate | 1 | — | 10 | — | — | 0 | 0 | 1 | 0 | 1 | 0 | 0 | 0 | — | — | 3 | — |
| 3. Methyl-N-(3-(N-(1,1-diethyl-propinyl)-carbamoyloxy)-phenyl)-carbamate | 1 | — | 10 | — | — | 0 | 0 | — | 0 | 0 | — | 1 | 0 | 0 | 1 | 1 | 0 |
| 4. Methyl-N-(3-(N-(1,1-dimethyl-propyl)-carbamoyloxy)-phenyl)-carbamate | 1 | — | 10 | 10 | 10 | 0 | 0 | 0 | 0 | 0 | 0 | 0 | 0 | 0 | 1 | 1 | 0 |
| 5. Methyl-N-(3-(N-(1,1-diethyl-propinyl)-carbamoyloxy)-phenyl)-carbamate | 1 | 10 | 10 | 10 | 10 | 3 | — | — | 0 | 4 | 3 | — | 0 | 3 | 4 | 1 | 0 |
| 6. Ethyl-N-(3-(N-(1,1-diethyl-propinyl)-carbamoyloxy)-phenyl)-carbamate | 1 | 10 | 10 | 10 | 10 | 3 | — | — | 0 | 4 | 3 | — | 0 | 3 | 4 | 1 | 0 |
| 7. Ethyl-N-(3-(N-1,1-dimethyl-propinyl)carbamoyloxy)-phenyl)-carbamate | 1 | 10 | 10 | 10 | 10 | 3 | 4 | — | 1 | 3 | 3 | — | — | 3 | 3 | 1 | — |
| 8. Ethyl-N-(3-(N-1,1-dimethyl-propyl)-carbamoyloxy)-phenyl)-carbamate | 1 | 10 | 10 | 10 | 10 | 2 | 5 | — | 0 | 3 | 0 | — | — | 0 | 4 | 4 | 2 |
| 9. S-Methyl-N-(3-(N-(1,1-diethylpropinyl)-carbamoyloxy)-phenyl)-thiocarbamate | 1 | 10 | 10 | 10 | 10 | 0 | 4 | — | 0 | 0 | 0 | 0 | 0 | 0 | 0 | 0 | 2 |
| 10. S-Methyl-N-(3-(N-(1,1-dimethyl-propinyl)-carbamoyloxy)-phenyl)-thio-carbamate | 1 | 10 | 10 | 10 | 10 | 0 | 2 | — | 0 | 0 | 0 | 0 | 0 | 0 | 0 | 0 | 2 |
| 11. S-Ethyl-N-(3-(N-(1-ethinylcyclohexyl)-carbumoyloxy)-phenyl)-thiocarbamate | 1 | 10 | 10 | 10 | 10 | 3 | 2 | — | 5 | 3 | 1 | 1 | 1 | — | 2 | 4 | 0 |
| 12. S-Ethyl-N-(3-(N-(1,1-diethyl-propinyl)-carbamoyloxy)-phenyl)-thiocarbamate | 1 | 8 | 10 | 10 | 10 | — | — | — | — | — | — | — | — | — | — | — | — |
| 13. S-Ethyl-N-(3-(N-(1,1-dimethyl-propinyl)-carbamoyloxy)-phenyl)-thiocarbamate | 1 | 10 | 10 | 10 | 10 | 2 | — | — | — | 3 | — | — | 0 | — | 1 | 2 | 2 |
| 14. S-Ethyl-N-(3-(N-(1-methylbutyl)-carbamoyloxy)-phenyl)-thio-carbamate | 1 | 10 | 10 | 10 | 10 | 4 | 1 | — | 7 | 2 | 0 | 1 | 0 | 6 | 1 | 5 | 1 |
| 15. S-Ethyl-N-(3-(N-(1-ethylpropyl)-carbamoyloxy)-phenyl)-thio-carbamate | 1 | 10 | 10 | 10 | 10 | 3 | 1 | 0 | 0 | 4 | 5 | 2 | 4 | 5 | 3 | 3 | 2 |
| 16. S-Methyl-N-(3-(N-(1-ethinyl-cyclohexyl)-carbamoyloxy)-phenyl)- | 1 | 10 | | | | | | | | | | | | | | | |

-continued

| | Applied quantity of kg active substance/ha | Cotton | Peanut | Corn | Rice | Stellaria media | Senecio vulgaris | Matricaria chamomilla | Lamium amplexicaule | Centaurea cyanus | Chrysanthemum segetum | Ipomea purpurea | Polygonum lapathifolium | Echinochloa crus galli | Setaria italica | Setaria faberi | Amarantus retroflexus |
|---|---|---|---|---|---|---|---|---|---|---|---|---|---|---|---|---|---|
| thiocarbamate | 1 | — | 10 | 10 | 10 | 0 | 0 | 0 | 0 | 0 | 0 | 0 | 0 | 1 | 1 | — | 0 |
| 17. S-Methyl-N-(3-(N-1-ethylpropyl)-carbamoyloxy)-phenyl)-thiocarbamate | 1 | 10 | 10 | 10 | 10 | 3 | — | 1 | 5 | 5 | — | — | 3 | — | 2 | — | 1 |
| 18. Methyl-N-(3-(N-(1-ethinilcyclohexyl)-phenyl)-carbamate | 1 | 10 | 10 | 10 | 10 | 0 | 0 | 0 | 0 | 0 | 0 | 1 | 0 | 0 | 1 | 1 | 1 |
| Comparison agent | | | | | | | | | | | | | | | | | |
| Isopropyl-N-phenylcarbamate | 1 | 10 | 10 | 10 | 10 | 7 | 10 | 10 | 10 | 10 | 10 | 10 | 10 | 10 | 10 | 10 | 10 |

0 = not damaged
10 = totally destroyed

What is claimed

1. A method for substantially preventing growth of weeds in plantings of cotton, which comprises applying to such planting in a past emergence manner a compound of the general formula

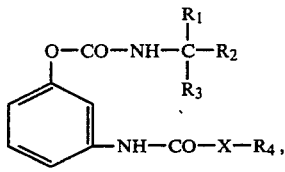

wherein
- $R_1$ is hydrogen or an alkyl radical of 1 to 3 carbons;
- $R_2$ is an alkyl, alkenyl or alkinyl radical of 1 to 4 carbons;
- $R_3$ is an alkyl radical of 1 to 3 carbons, or $R_1$ and $R_3$ with the carbon atom represent a cycloaliphatic group with 5 or 6 carbons;
- $R_4$ is an alkyl group of 1 to 3 carbons; and
- X is sulfur, in an amount of from about 0.5 to 5 kilograms per hectare.

2. A method as defined in claim 1, wherein said compound is S-methyl-N-(3-(N-(1,1-diethylpropinyl)carbamoyloxy)-phenyl)-thiocarbamate.

3. A method as defined in claim 1, wherein said compound is S-methyl-N-(3-(N-(1,1-dimethylpropyl)carbamoyloxy)-phenyl)-thiocarbamate.

4. A method as defined in claim 1, wherein said compound is S-ethyl-N-(3-(N-(1-ethinylcyclohexyl)carbamoyloxy)-phenyl)-thiocarbamate.

5. A method as defined in claim 1, wherein said compound is S-ethyl-N-(3-(N-(1,1-diethylpropinyl)carbamoyloxy)-phenyl)-thiocarbamate.

6. A method as defined in claim 1, wherein said compound is S-ethyl-N-(3-(N-(1,1-dimethylpropinyl)carbamoyloxy)-phenyl)-thiocarbamate.

7. A method as defined in claim 1, wherein said compound is S-ethyl-N-(3-(N-(1-methylbutyl)-carbamoyloxy)-phenyl)-thiocarbamate.

8. A method as defined in claim 1, wherein said compound is S-ethyl-N-(3-(N-(1-ethylpropyl)-carbamoyloxy)-phenyl)-thiocarbamate.

9. A method as defined in claim 1, wherein said compound is S-methyl-N-(3-(N-(1-ethinylcyclohexyl)carbamoyloxy)-phenyl)-thiocarbamate.

10. A method as defined in claim 1, wherein said compound is S-methyl-N-(3-(N-(1-ethylpropyl)-carbamoyloxy)-phenyl)-thiocarbamate.